United States Patent
Capelli et al.

(10) Patent No.: US 12,357,018 B2
(45) Date of Patent: Jul. 15, 2025

(54) NICOTINE GEL

(71) Applicant: Philip Morris Products S.A., Neuchatel (CH)

(72) Inventors: Sebastien Capelli, Neuchatel (CH); Farideh Goudarzi, Cambridge (GB); Timothy King, Cambridge (GB); Jean-Yves Vollmer, Neuchatel (CH); Gerard Zuber, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 18/637,390

(22) Filed: Apr. 16, 2024

(65) Prior Publication Data

US 2024/0268444 A1 Aug. 15, 2024

Related U.S. Application Data

(63) Continuation of application No. 17/040,232, filed as application No. PCT/EP2019/058845 on Apr. 8, 2019, now Pat. No. 11,980,219.

(30) Foreign Application Priority Data

Apr. 6, 2018 (EP) .................................... 18166166

(51) Int. Cl.
| | | |
|---|---|---|
| A24B 15/167 | (2020.01) | |
| A24B 15/32 | (2006.01) | |
| A24B 15/40 | (2006.01) | |
| A61K 9/00 | (2006.01) | |
| A61K 9/06 | (2006.01) | |
| A61K 31/465 | (2006.01) | |
| A61K 36/185 | (2006.01) | |
| A61K 47/02 | (2006.01) | |
| A61K 47/10 | (2017.01) | |
| A61K 47/12 | (2006.01) | |
| A61K 47/36 | (2006.01) | |
| A61K 47/46 | (2006.01) | |

(52) U.S. Cl.
CPC .......... *A24B 15/167* (2016.11); *A24B 15/32* (2013.01); *A24B 15/403* (2013.01); *A61K 9/007* (2013.01); *A61K 9/06* (2013.01); *A61K 31/465* (2013.01); *A61K 36/185* (2013.01); *A61K 47/02* (2013.01); *A61K 47/10* (2013.01); *A61K 47/12* (2013.01); *A61K 47/36* (2013.01); *A61K 47/46* (2013.01)

(58) Field of Classification Search
CPC ...... A24B 15/167; A24B 15/32; A24B 15/403
USPC ......................................................... 131/328
See application file for complete search history.

(56) References Cited

U.S. PATENT DOCUMENTS

| | | | |
|---|---|---|---|
| 4,746,528 A | 5/1988 | Prest et al. | |
| 5,891,199 A * | 4/1999 | Wachter ................. | A61K 8/736 8/405 |
| 6,080,783 A | 6/2000 | Davidson et al. | |
| 6,110,495 A | 8/2000 | Dam | |
| 6,365,624 B1 | 4/2002 | Davidson et al. | |
| 6,602,996 B1 | 8/2003 | Sworn et al. | |
| 6,673,835 B1 | 1/2004 | Hensley et al. | |
| 8,231,921 B2 * | 7/2012 | Bezanson ............... | C12P 19/04 426/576 |
| 2002/0032231 A1 | 3/2002 | Davidson et al. | |
| 2004/0109895 A1 | 6/2004 | Hensley et al. | |
| 2005/0118243 A1 | 6/2005 | Hensley et al. | |
| 2007/0265337 A1 | 11/2007 | Hensley et al. | |
| 2007/0269386 A1 | 11/2007 | Steen et al. | |
| 2008/0145505 A1 * | 6/2008 | Bezanson ................. | A23L 2/52 426/660 |
| 2010/0063110 A1 | 3/2010 | Meyer et al. | |
| 2011/0077296 A1 | 3/2011 | Hensley et al. | |
| 2014/0096781 A1 * | 4/2014 | Sears ...................... | A24F 40/53 131/328 |
| 2016/0120225 A1 | 5/2016 | Mishra et al. | |
| 2016/0331032 A1 * | 11/2016 | Malgat .................. | A24F 40/465 |
| 2018/0029782 A1 * | 2/2018 | Zuber ..................... | A24F 40/42 |
| 2019/0261684 A1 * | 8/2019 | Reevell .................. | A24F 40/46 |

FOREIGN PATENT DOCUMENTS

| | | |
|---|---|---|
| CN | 101933653 B | 10/2012 |
| CN | 103960783 A | 8/2014 |
| CN | 103960784 A | 8/2014 |
| CN | 104256888 8 | 6/2016 |
| CN | 106998811 A | 8/2017 |
| CN | 107126411 A | 9/2017 |
| JP | 2009-524573 A | 7/2009 |
| JP | 2015-536688 A | 12/2015 |
| JP | 2016-528930 A | 9/2016 |
| JP | 2016-536982 A | 12/2016 |
| RU | 2 519 959 C2 | 8/2014 |
| RU | 2020 132 930 A | 5/2022 |
| RU | 2020 132 934 A | 5/2022 |
| WO | WO 00/12081 A1 | 3/2000 |

(Continued)

OTHER PUBLICATIONS

International Search Report and Written Opinion issued on Jul. 4, 2019 in PCT/EP2019/058845 filed on Apr. 8, 2019.

(Continued)

*Primary Examiner* — Peter G Leigh

(74) *Attorney, Agent, or Firm* — Oblon, McClelland, Maier & Neustadt, L.L.P.

(57) ABSTRACT

A composition is provided, including a gelling agent forming a solid medium, glycerol dispersed in the solid medium; and nicotine dispersed in the glycerol.

6 Claims, No Drawings

(56) References Cited

FOREIGN PATENT DOCUMENTS

| WO | WO 2008/112124 A2 | 9/2008 | |
|---|---|---|---|
| WO | WO 2014/083333 A1 | 6/2014 | |
| WO | WO 2014/126985 A1 | 8/2014 | |
| WO | WO 2016/063423 A1 | 4/2016 | |
| WO | WO 2016/069903 A1 | 5/2016 | |
| WO | WO-2016069876 A1 * | 5/2016 | ............. A24B 13/00 |
| WO | WO 2016/133109 A1 | 8/2016 | |
| WO | WO 2017/051006 A1 | 3/2017 | |
| WO | WO 2017/051011 A1 | 3/2017 | |
| WO | WO 2017/051016 A1 | 3/2017 | |
| WO | WO-2017087606 A1 * | 5/2017 | |
| WO | WO 2018/019543 A1 | 2/2018 | |
| WO | WO-2018019738 A1 * | 2/2018 | ............. A24F 40/00 |
| WO | WO 2019/129470 | 7/2019 | |
| WO | WO 2019/193209 A1 | 10/2019 | |
| WO | WO 2019/193210 A1 | 10/2019 | |

OTHER PUBLICATIONS

Masakuni Tako, "The Principle of Polysaccharide Gels" Advances in Bioscience and Biotechnology, vol. 6, 2015, pp. 22-36.

Russian Office Action and Search Report issued on Sep. 21, 2022 in Russian Patent Application No. 20201354402 (with English translation), 26 pages.

Bagirova et al., "Current aspects of the use of excipients as exemplified by transdermal therapeutic system technology", Pharmateca, 1998, No. 6, 7 pages.

Tentsova et al., "Current biopharmaceutical aspects of excipients", Pharmacy, 2012, No. 7, pp. 1-14.

Tikhonov, "Drug technology: Textbook for pharmaceutical universities and faculty", Kh., NFAU, Golden Pages, 2002, pp. 1-670 (679 total pages).

Mexican Office Action issued Dec. 13, 2022 in Mexican Patent Application No. MX/A/2020/010160 (with English translation), 13 pages.

Petri, "Xanthan gum: A versatile biopolymer for biomedical and technological applications", Journal of Applied Polymer Science, vol. 132, No. 23, 2015, pp. 1-13.

Russian Office Action issued on Jan. 31, 2023 in Russian Patent Application No. 2020135402 (with English translation), 17 pages.

Combined Chinese Office Action and Search Report issued on Mar. 30, 2023 in Chinese Patent Application No. 201980017846.7 (with English translation), 14 pages.

Japanese Office Action issued on Feb. 15, 2023 in Japanese Patent Application No. 2020-550688 (with English translation), 18 pages.

Russian Office Action issued May 23, 2023 in Russian Patent Application No. 2020135402/04 (with English Translation), 22 pages.

"Thickeners and Gelling Agents", retrieved from https://produkt.by/story/zagustiteli.igeleovrazovateli, Dec. 28, 2016, 22 pages.

Combined Brazilian Office Action and Search Report issued Aug. 1, 2023 in Brazilian Patent Application No. 112020017480-7 (with English Translation of Office Action Only), 5 pages.

Office Action issued Oct. 31, 2024, in corresponding Japanese Patent Application No. 2023-203631 (with English Translation), 11 pages.

Office Action issued Mar. 10, 2025, in corresponding Japanese Patent Application No. 2020-550688.

* cited by examiner

NICOTINE GEL

CROSS REFERENCE TO RELATED APPLICATIONS

This application is a continuation of and claims benefit under 35 U.S.C. § 120 to U.S. application Ser. No. 17/040,232, filed on Sep. 22, 2020, which is a U.S. national stage application of PCT/EP2019/058845, filed on Apr. 8, 2019, and claims the benefit of priority under 35 U.S.C. § 119 from EP Application No. 18166166.1, filed on Apr. 6, 2018, the entire contents of which are incorporated herein by reference.

TECHNICAL FIELD

This disclosure relates to nicotine gel that is stable and may be utilized with an aerosol-generating device.

DESCRIPTION OF THE RELATED ART

Nicotine compositions for use with aerosol-generating articles are known. Often the nicotine composition is a liquid composition, such as an e-liquid, that is heated by a coiled electrically resistive filament of an aerosol-generating article. To avoid accidental leakage of the liquid composition, a good deal of care is taken to manufacture the containers holding this liquid composition.

Use of alternative forms of compositions comprising nicotine may reduce potential leakage concerns. However, these alternative forms of compositions comprising nicotine are not often stable. In particular, gel forms of compositions comprising nicotine may release a liquid phase upon storage or from manufacture to consumption by the user.

It would be desirable to provide a gel composition comprising nicotine that was physically stable. It would be desirable to provide a gel composition comprising nicotine that was physically stable over a broad range of storage conditions. It would be desirable to provide a gel composition comprising nicotine that did not release liquid phase. It would be desirable to provide a gel composition comprising nicotine that did not absorb liquid phase. It would be desirable to provide a stable gel phase composition that vaporizes nicotine within the composition upon heating. It would be desirable to provide a gel composition comprising nicotine that did not leak out of an aerosol-generating device.

SUMMARY

Various aspects of the disclosure relate to physically stable gel phase nicotine compositions. These physically stable gel phase nicotine compositions may not release or absorb water over a broad range of relative humidifies (such as from about 10% to about 60% relative humidity, for example). The physically stable gel phase nicotine composition's mass may not change by more than about 20%, or may not change by more than about 15%, or may not change by more than about 10%, when exposed to a variety of environmental conditions. The composition may have an exterior shape with an exposed surface area that does not change by more than about 10%, or does not change by more than about 5%, or does not change by more than about 1%, when exposed to a variety of environmental conditions. The stable gel phase compositions include nicotine, an aerosol former, and a gelling agent.

DETAILED DESCRIPTION

In one aspect of the disclosure, a composition includes a gelling agent forming a solid medium, glycerol dispersed in the solid medium, and nicotine dispersed in the glycerol. The composition is a stable gel phase.

In another aspect of the disclosure, the composition includes at least about 70% to about 95% wt. glycerol. In many of these aspects the composition includes water at less than about 22% wt. and the total weight of water and glycerol is in a range from about 90 to 95% wt. In some of these aspects the composition is substantially free of water.

In one or more aspects, the composition includes the gelling agent in a range from about 2.5% to about 5% by weight. In many of these aspects the gelling agent includes xanthan gum. The gelling agent may include agar, xanthan gum, and low acyl gellan. The gelling agent may include agar, xanthan gum, and low acyl gellan in substantially equal amounts.

In one or more aspects, the composition has a mass and the mass does not change by more than about 20%, or does not change by more than about 15%, or does not change by more than about 10%, when exposed to a relative humidity in a range from about 10% to about 60% at 24 degrees Celsius and one atmosphere.

In one or more aspects, the composition has an exterior shape with an exposed surface area that does not change by more than about 10%, or does not change by more than about 5%, or does not change by more than about 1%, when exposed to a relative humidity in a range from about 10% to about 60% at 24 degrees Celsius and one atmosphere In one or more aspects, the composition has an exposed surface area value and a mass value, the mass value to exposed surface area value is in a range from about 0.5:1 to about 1:0.1, or from about 0.5:1 to about 1:0.5.

In one or more aspects, the composition includes: about 1.5 to about 2.5% wt. nicotine; about 90 to about 95% wt. glycerol; about 2 to about 4% wt. agar, xanthan gum and low acyl gellan; levulinic acid; and calcium ions, and the composition is substantially free of water.

In one or more aspects, the composition includes: about 1.5 to about 2.5% wt. nicotine; about 70 to about 75% wt. glycerol; about 18 to about 22% wt. water; about 2 to about 4% wt. agar, xanthan gum and low acyl gellan; levulinic acid; and calcium ions.

Advantageously, a stable gel composition comprising nicotine provides predictable composition form upon storage or transit from manufacture to the consumer. The stable gel composition comprising nicotine substantially maintains its shape. The stable gel composition comprising nicotine substantially does not release a liquid phase upon storage or transit from manufacture to the consumer. The stable gel composition comprising nicotine may provide for a simple consumable design. This consumable may not have to be designed to contain a liquid, thus a wider range of materials and container constructions may be contemplated.

The gel composition described herein may be combined with an aerosol-generating device to provide a nicotine aerosol to the lungs at inhalation or air flow rates that are within conventional smoking regime inhalation or air flow rates. The aerosol-generating device may continuously heat the gel composition. A consumer may take a plurality of inhalations or "puffs" where each "puff" delivers an amount of nicotine aerosol. The gel composition may be capable of delivering a high nicotine/low total particulate matter (TPM) aerosol to a consumer when heated, preferably in a continuous manner.

The term "nicotine" refers to nicotine and nicotine derivatives such as free-base nicotine, nicotine salts and the like.

The phrase "stable gel phase" or "stable gel" refers to gel that substantially maintains its shape and mass when exposed to a variety of environmental conditions. The stable gel may not substantially release (sweat) or absorb water when exposed to a standard temperature and pressure while varying relative humidity from about 10% to about 60%. For example, the stable gel may substantially maintain its shape and mass when exposed to a standard temperature and pressure while varying relative humidity from about 10% to about 60%.

The gel composition described herein may be combined with an aerosol-generating device to deliver nicotine to a consumer. The gel composition may be packaged separately (as a gel consumable) from or not form a portion of the aerosol-generating device. A depleted gel consumable may be replaced with a full charged gel consumable within the aerosol-generating device. A plurality of these gel consumables may be combined with an aerosol-generating device to form a kit.

The gel composition described herein may be packaged in a sealed or closed container for transit from manufacture to consumption by the consumer. The gel composition has an exposed surface that is in contact with a head space defined by the interior surface of the container. The head space may have a relative humidity that equilibrates with the gel composition. The head space relative humidity may be substantially similar to the (local) humidity provided by the gel composition.

A composition, according to the disclosure, includes a gelling agent forming a solid medium, glycerol dispersed in the solid medium, and nicotine dispersed in the glycerol. The composition is a stable gel phase.

The stable gel composition has a mass and the mass does not change by more than about 20%, or does not change by more than about 15%, or does not change by more than about 10%, when exposed to a relative humidity in a range from about 10% to about 60% at 24 degrees Celsius and one atmosphere.

The stable gel composition has an exterior shape with an exposed surface area that does not change by more than about 10%, or does not change by more than about 5%, or does not change by more than about 1%, when exposed to a relative humidity in a range from about 10% to about 60% at 24 degrees Celsius and one atmosphere The stable gel composition has an exposed surface area value and a mass value, the mass value to exposed surface area value is in a range from about 0.5:1 to about 1:0.1, or from about 0.5:1 to about 1:0.5.

One exemplary gel composition article has a height of about 5.8 mm, a diameter of about 6.6 mm and a weight of about 200 to about 220 mg. The exposed surface area of this solid cylinder (less the circular end contacting a substrate) is about 325 mm$^2$. Thus, the mass value to exposed surface area value is about 1:0.66. Reducing the exposed surface area may improve the stability of the gel composition. However, reducing the exposed surface area value also reduces the mass transport of the nicotine into a vapor phase from the gel composition.

Preferably the gel composition includes a specific ratio of water to glycerol content to maintain an equilibrated local humidity with ambient environmental humidity. This range of water to glycerol content may provide the properties needed to maintain a stable gel composition. The stable gel composition will not substantially flow and substantially maintains its shape over time. The stable gel composition will not substantially flow and substantially maintains its mass over time. The stable gel will not substantially release water (sweat) or absorb water over time when exposed to ambient environmental conditions.

Depending on the ratio weight/weight of glycerol and water, the gel composition will create its own local relative humidity in equilibrium with the surrounding ambient environment in a closed system. When the gel composition is exposed to a lower surrounding ambient environment relative humidity than the local relative humidity of the gel composition, the gel composition will dry. When the gel composition is exposed to a higher surrounding ambient environment relative humidity than the local relative humidity of the gel composition, the gel composition will create a liquid phase. This liquid phase is not desirable. When the gel composition is exposed to a similar surrounding ambient environment relative humidity as the local relative humidity of the gel composition, certain gel compositions appear to be stable. Thus, selecting the proper ratio weight/weight of glycerol and water for creating equality in the equilibrium relative humidity and the surrounding ambient environment relative humidity, in addition to selecting proper gelling agents both assist in providing a stable gel composition.

The relationship between glycerol concentration, measured by specific gravity, and the equilibrium relative humidity at forms at 24 degrees Celsius in a closed system is described by the following equation:

$$SG = [-0.189(RH) + 19.9]^{0.0806}$$

where RH is the desired percent relative humidity and SG is the specific gravity of the glycerol-water solution needed to produce this relative humidity. Ratios of water and glycerol needed to produce a desired specific gravity (SG) may be calculated from the following equation:

$$G_W = 383(SG) - 383$$

where $G_W$ is the percent glycerol by weight of the solution.

The relationship of specific gravity (SG) of water-glycerol solutions and equilibrium relative humidity (RH) at 24 degrees Celsius may be calculated from the following equation:

$$RH = \frac{-(SG^{12.4} - 19.9)}{0.189}$$

This equation has a curve fit of r=0.998. The equilibrium relative humidity decreases slowly as the glycerol content increases, but changes more rapidly when the glycerol content exceeds about 70% wt. Thus, equilibrium relative humidity may be controlled by selecting the composition of the glycerol-water solution used to form the gel composition.

The composition may have an equilibrium relative humidity of at least 10%. The composition may have an equilibrium relative humidity in a range from about 10% to about 60%. The composition may have an equilibrium relative humidity in a range from about 10% to about 55%. The composition may have an equilibrium relative humidity in a range from about 25% to about 50%.

The composition may include at least about 70% to about 95% wt. glycerol. In many of these aspects the composition includes water at less than about 22% wt. and the total weight of water and glycerol is in a range from about 90 to 95% wt. In some of these aspects the composition is substantially free of water.

The composition may include from about 90% to about 95% wt. glycerol and be free of water, or substantially free of water. In other aspects the composition may include from about 70% to about 75% wt. glycerol and water from about 20% to about 25% wt. In other aspects the composition may include from about 70% to about 75% wt. glycerol and water from about 20% to about 25% wt., and have a total water and glycerol content from about 90 to about 95% wt.

The composition includes the gelling agent in a range from about 2% to about 7% by weight. The composition includes the gelling agent in a range from about 2.5% to about 5% by weight. The composition includes the gelling agent in a range from about 2.5% to about 3.5% by weight.

The composition includes the gelling agent that forms the solid medium or support matrix of the stable gel composition. The gelling agent may include one or more biopolymers. The biopolymers may be formed of polysaccharides.

Biopolymers include, for example, gellan gums (native, low acyl gellan gum, high acyl gellan gums with low acyl gellan gum being preferred), xanthan gum, alginates (alginic acid), agar, guar gum, and the like. The composition may preferably include xanthan gum. The composition may include two biopolymers. The composition may include three biopolymers. The composition may include the two biopolymers in substantially equal weights. The composition may include the three biopolymers in substantially equal weights.

The composition may preferably include xanthan gum. The composition may include xanthan gum in a range from about 2% to about 5% wt., or in a range from about 2% to about 4% wt., or about 3% wt.

The composition may preferably include xanthan gum, gellan gum, and agar. The composition may include xanthan gum, low acyl gellan gum, and agar. The composition may include xanthan gum, gellan gum, and agar in substantially equal weights. The composition may include xanthan gum, low acyl gellan gum, and agar in substantially equal weights. The composition may include xanthan gum, low acyl gellan gum, and agar in a range from about 2% to about 5% wt., or in a range from about 2% to about 4% wt., or about 3% wt. The composition may include xanthan gum, low acyl gellan gum, and agar in a range from about 2% to about 5% wt., or in a range from about 2% to about 4% wt., or about 3% wt., where xanthan gum, gellan gum, and agar are substantially equal weights.

The composition may include a divalent cation. Preferably the divalent cation includes calcium ions, such as calcium lactate in solution. Divalent cations (such as calcium ions) may assist in the gel formation of compositions that include biopolymers (polysaccharides) such as, gellan gums (native, low acyl gellan gum, high acyl gellan gums), xanthan gum, alginates (alginic acid), agar, guar gum, and the like. The ion effect may assist in the gel formation. The divalent cation may be present in the gel composition in a range from about 0.1 to about 1% by weight, or about 0.5% wt.

The composition may include a carboxylic acid. The carboxylic acid may include a ketone group. Preferably the carboxylic acid may include a ketone group having less than 10 carbon atoms. Preferably this carboxylic acid has five carbon atoms (such as levulinic acid). Levulinic acid may be added to neutralize the pH of the nicotine gel. This may also assist in the gel formation that includes biopolymers (polysaccharides) such as, gellan gums (low acyl gellan gum, high acyl gellan gums), xanthan gum, especially alginates (alginic acid), agar, guar gum, and the like. Levulinic acid may also enhance a sensory profile of the gel formulation.

Nicotine is included in the gel compositions. The nicotine may be added to the composition in a free base form or a salt form. The gel composition includes about 1 to about 3% wt., or about nicotine, or about 1.5 to about 2.5% wt., or about 2% wt. nicotine. The nicotine component of the gel formulation may be the most volatile component of the gel formulation. In some aspects water may be the most volatile component of the gel formulation and the nicotine component of the gel formulation may be the second most volatile component of the gel formulation.

The gel composition may include: about 1 to about 3% wt. nicotine; about 90 to about 95% wt. glycerol; about 2 to about 4% wt. gelling agent; levulinic acid; and calcium ions, and the composition is substantially free of water.

The gel composition may include: about 1 to about 3% wt. nicotine; about 90 to about 95% wt. glycerol; about 2 to about 4% wt. xanthan gum; levulinic acid; and calcium ions, and the composition is substantially free of water.

The gel composition may include: about 1 to about 3% wt. nicotine; about 90 to about 95% wt. glycerol; about 2 to about 4% wt. agar, xanthan gum and low acyl gellan; levulinic acid; and calcium ions, and the composition is substantially free of water.

The gel composition may include: about 1.5 to about 2.5% wt. nicotine; about 90 to about 95% wt. glycerol; about 2 to about 4% wt. agar, xanthan gum and low acyl gellan; levulinic acid; and calcium ions, and the composition is substantially free of water. The agar, xanthan gum and low acyl gellan, may be present in substantially equal weights.

The gel composition may include: about 1 to about 3% wt. nicotine; about 70 to about 75% wt. glycerol; about 18 to about 22% wt. water; about 2 to about 4% wt. gelling agent; levulinic acid; and calcium ions.

The gel composition may include: about 1 to about 3% wt. nicotine; about 70 to about 75% wt. glycerol; about 2 to about 4% wt. xanthan gum; levulinic acid; and calcium ions.

The gel composition may include: about 1 to about 3% wt. nicotine; about 70 to about 75% wt. glycerol; about 18 to about 22% wt. water; about 2 to about 4% wt. agar, xanthan gum and low acyl gellan; levulinic acid; and calcium ions.

The gel composition may include: about 1.5 to about 2.5% wt. nicotine; about 70 to about 75% wt. glycerol; about 18 to about 22% wt. water; about 2 to about 4% wt. agar, xanthan gum and low acyl gellan; levulinic acid; and calcium ions. The agar, xanthan gum and low acyl gellan, may be present in substantially equal weights.

The gel composition may be heated (via an aerosol-generating device) to vaporize nicotine. Heating the gel composition may not release a liquid phase.

All scientific and technical terms used herein have meanings commonly used in the art unless otherwise specified. The definitions provided herein are to facilitate understanding of certain terms used frequently herein.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

Examples

Table 1 describes gel composition formulations that were formulated.

TABLE 1

| Example | Formulation (w/w) | Change in Shape at Ambient RH |
|---|---|---|
| 1 | 0.5% Low Acyl Gellan<br>0.5% Guar<br>2% Nicotine<br>0.5% Calcium<br>1.3% Levulinic acid<br>95.2% Glycerol | Yes |
| 2 | 0.5% Low Acyl Gellan<br>0.5% Guar<br>2% Nicotine<br>0.5% Calcium<br>1.3% Levulinic acid<br>85.2% Glycerol<br>10% Water | Yes |
| 3 | 1% Low Acyl Gellan<br>1% Agar<br>1% Xanthan<br>2% Nicotine<br>1% Calcium<br>1.3% Levulinic acid<br>92.7% Glycerol | Slight |
| 4 | 1% Low Acyl Gellan<br>1% Xanthan<br>1% Agar<br>2% Nicotine<br>0.5% Calcium<br>1.3% Levulinic acid<br>20% Water<br>72.7% Glycerol | No |
| 5 | 2% Low Acyl Gellan<br>1% Xanthan<br>2% Nicotine<br>0.5% Calcium<br>1.3% Levulinic acid<br>20% Water<br>72.7% Glycerol | No |
| 6 | 1.5% Low Acyl Gellan<br>1.5% High Acyl Gellan<br>2% Nicotine<br>1% Calcium<br>1.3% Levulinic acid<br>72.7% Glycerol | No |
| 7 | 1% Alginate<br>1% Xanthan<br>1% Agar<br>2% Nicotine<br>1% Calcium<br>1.3% Levulinic acid<br>20% Water<br>72.7.2% Glycerol | No |
| 8 | 3% Low Acyl Gellan<br>2% Nicotine<br>1% Calcium<br>1.3% Levulinic acid<br>20% Water<br>72.7.2% Glycerol | No |
| 9 | 1% Agar<br>2% Nicotine<br>1.3% Levulinic acid<br>30% Water<br>65.7% Glycerol | — |

Indentation Test

Measurements were conducted using an Anton Parr PNR12 penetrometer and a quarter-cone plate. Samples (gel compositions) were loaded under the needle and aligned manually with the top of the sample surface. The tip of the needle's shadow on the sample was brought into contact with the needle. At least three measurements were conducted per sample. The mean distance penetrated for each gel was measured.

Example 1 had a distance penetrated of about 7.5 mm.
Example 2 had a distance penetrated of about 7.7 mm.
Example 3 had a distance penetrated of about 7.0 mm.
Example 4 had a distance penetrated of about 3.8 mm.
Example 9 had a distance penetrated of about 5.0 mm.

The greater the distance penetrated, the softer the gel composition.

Gel Composition Weight Change Over Time

The weights of several example formulations were evaluated over 45 days at various relative humidities. A stable gel composition will substantially maintain its initial weight over the 45 days.

Example 4 was weighed over 45 days at three relative humidity levels (10%, 60% and 70%). At 60% relative humidity, this gel composition added about 10% to its weight over the 45 days with nearly all of the weight gain occurring in the first 5 days. At 10% relative humidity, this gel composition lost about 15% to its weight over the 45 days with nearly all of the weight loss occurring in the first 5 days. At 70% relative humidity, this gel composition added about 25% to its weight over the 45 days with nearly all of the weight gain occurring in the first 5 days. At all three relative humidity levels (10%, 60% and 70%) no liquid phase was observed.

Example 2 was weighed over 45 days at three relative humidity levels (10%, 60% and 70%). At 60% relative humidity, this gel composition added about 15% to its weight over the 45 days with nearly all of the weight gain occurring in the first 5 days. At 10% relative humidity, this gel composition lost about 5% to its weight over the 45 days with nearly all of the weight loss occurring in the first 5 days. At 70% relative humidity, this gel composition added about 45% to its weight over the 45 days with nearly all of the weight gain occurring in the first 5 days. However, at all three relative humidity levels (10%, 60% and 70%) a liquid phase was observed.

The invention claimed is:
1. A composition, comprising:
a gelling agent in a range from about 2% to about 5% by weight, the gelling agent forming a solid medium;
glycerol in a range of about 70% to about 95% by weight, the glycerol being dispersed in the solid medium;
nicotine in an amount of about 1.5 to about 3% by weight, the nicotine being dispersed in the glycerol;

divalent cations in a range from about 0.1 to about 1% by weight:
a carboxylic acid; and
water at less than about 22% by weight,
wherein the gelling agent comprises one or more biopolymers selected from a low acyl gellan, a high acyl gellan, a xanthan gum, an alginate, an agar and a guar gum, and
wherein the total weight of the water and glycerol is in a range from about 90 to 95% by weight.

2. The composition of claim 1, wherein the composition has an equilibrium relative humidity at 24 degrees Celsius and one atmosphere in a range from about 10% to about 60%, wherein equilibrium relative humidity may be calculated from equation (I) below:

$$RH = \frac{-\left(\left(\frac{G_w}{383}+1\right)^{12.4} - 19.9\right)}{0.189} \quad (I)$$

wherein RH is the equilibrium relative humidity and $G_W$ is the percent glycerol by weight.

3. The composition of claim 1 wherein the gelling agent comprises agar, xanthan gum, and low acyl gellan in substantially equal amounts.

4. The composition of claim 1, wherein the composition further comprises levulinic acid.

5. The composition of claim 1, wherein the composition comprises about 1.5 to about 2.5% wt. nicotine.

6. The composition of claim 1 comprising:
about 1.5 to about 2.5% wt. nicotine;
about 70 to about 75% wt. glycerol;
about 18 to about 22% wt. water;
about 2 to about 4% wt. agar, xanthan gum and low acyl gellan;
levulinic acid; and
calcium ions.

* * * * *